(12) United States Patent
Nelson et al.

(10) Patent No.: US 12,091,818 B2
(45) Date of Patent: *Sep. 17, 2024

(54) PROCESSES FOR PRODUCING NANOCELLULOSE, AND NANOCELLULOSE COMPOSITIONS PRODUCED THEREFROM

(71) Applicant: GranBio Intellectual Property Holdings, LLC, Minnetrista, MN (US)

(72) Inventors: Kimberly Nelson, Atlanta, GA (US); Theodora Retsina, Atlanta, GA (US)

(73) Assignee: GranBio Intellectual Property Holdings, LLC, Thomaston, GA (US)

( * ) Notice: Subject to any disclaimer, the term of this patent is extended or adjusted under 35 U.S.C. 154(b) by 110 days.

This patent is subject to a terminal disclaimer.

(21) Appl. No.: 17/209,388

(22) Filed: Mar. 23, 2021

(65) Prior Publication Data

US 2021/0277151 A1 Sep. 9, 2021

Related U.S. Application Data

(63) Continuation of application No. 15/278,800, filed on Sep. 28, 2016, now abandoned.
(Continued)

(51) Int. Cl.
*D21C 9/00* (2006.01)
*C07G 1/00* (2011.01)
(Continued)

(52) U.S. Cl.
CPC .............. *D21C 9/007* (2013.01); *C07G 1/00* (2013.01); *C08B 15/08* (2013.01);
(Continued)

(58) Field of Classification Search
CPC . D21C 9/007; D21C 1/02; D21B 1/12; D21B 1/14; D21B 1/36; D21B 1/38; D21H 11/16; D21H 11/18
See application file for complete search history.

(56) References Cited

U.S. PATENT DOCUMENTS

| | | | |
|---|---|---|---|
| 5,769,934 A * | 6/1998 | Ha | C08B 15/02 536/56 |
| 9,322,133 B2 * | 4/2016 | Nelson | C12P 7/14 |

(Continued)

FOREIGN PATENT DOCUMENTS

| | | | |
|---|---|---|---|
| JP | 2006136263 A * | 6/2006 | |
| JP | 5398180 B2 * | 1/2014 | |

OTHER PUBLICATIONS

Smook, Handbook for Pulp and Paper Technologists, 1992, Angus Wilde Publications, 2nd edition, chapters 4 and 5 (Year: 1992).*
(Continued)

*Primary Examiner* — Anthony Calandra
(74) *Attorney, Agent, or Firm* — O'Connor & Company; Ryan P. O'Connor

(57) ABSTRACT

Various processes are disclosed for producing nanocellulose materials following steam extraction or hot-water digestion of biomass. Processes are also disclosed for producing nanocellulose materials from a wide variety of starting pulps or pretreated biomass feedstocks. The nanocellulose materials may be used as rheology modifiers in many applications. Water-based and oil-based drilling fluid formulations and additives are provided. Also, water-based and oil-based hydraulic fracturing fluid formulations and additives are provided. In other embodiments, polymer-nanocellulose composites are provided.

14 Claims, 6 Drawing Sheets

Related U.S. Application Data

(60) Provisional application No. 62/235,052, filed on Sep. 30, 2015.

(51) Int. Cl.

| | | |
|---|---|---|
| *C08B 15/08* | (2006.01) | |
| *C08B 37/00* | (2006.01) | |
| *C12P 7/10* | (2006.01) | |
| *D21B 1/06* | (2006.01) | |
| *D21B 1/12* | (2006.01) | |
| *D21B 1/14* | (2006.01) | |
| *D21C 1/02* | (2006.01) | |
| *D21C 5/00* | (2006.01) | |
| *D21C 11/00* | (2006.01) | |
| *D21H 11/16* | (2006.01) | |
| *D21H 11/18* | (2006.01) | |
| *C08H 8/00* | (2010.01) | |
| *C09K 8/10* | (2006.01) | |
| *C09K 8/34* | (2006.01) | |
| *C09K 8/64* | (2006.01) | |
| *C09K 8/68* | (2006.01) | |
| *C13K 1/02* | (2006.01) | |
| *D21C 3/00* | (2006.01) | |
| *D21C 3/06* | (2006.01) | |
| *D21C 9/10* | (2006.01) | |

(52) U.S. Cl.
CPC ............ *C08B 37/0057* (2013.01); *C12P 7/10* (2013.01); *D21B 1/061* (2013.01); *D21B 1/12* (2013.01); *D21B 1/14* (2013.01); *D21C 1/02* (2013.01); *D21C 5/005* (2013.01); *D21C 11/0007* (2013.01); *D21H 11/16* (2013.01); *D21H 11/18* (2013.01); *C08H 8/00* (2013.01); *C09K 8/10* (2013.01); *C09K 8/34* (2013.01); *C09K 8/64* (2013.01); *C09K 8/68* (2013.01); *C13K 1/02* (2013.01); *D21C 3/003* (2013.01); *D21C 3/006* (2013.01); *D21C 3/06* (2013.01); *D21C 9/10* (2013.01)

(56) References Cited

U.S. PATENT DOCUMENTS

| | | | |
|---|---|---|---|
| 2009/0221812 A1* | 9/2009 | Ankerfors | D21H 11/18 162/28 |
| 2014/0154757 A1* | 6/2014 | Nelson | D21C 9/002 536/56 |
| 2014/0249237 A1* | 9/2014 | Ferraro | C10G 2/32 422/162 |

OTHER PUBLICATIONS

Osong et al., Mechanical Pulp Based Nano-ligno-cellulose:Production, Characterization and their Effect on Paper Properties, Apr. 2014,Mi-Sweden University. (Year: 2014).*

Sundholm (editor), Mechanical Pulping, Fapet Oy, 1999, p. 157-161, 190-195, and 200-201 (Year: 1999).*

Machine English Translation JP-5398180-B2, Jan. 29, 2014 (Year: 2014).*

* cited by examiner

PROCESSES FOR PRODUCING NANOCELLULOSE, AND NANOCELLULOSE COMPOSITIONS PRODUCED THEREFROM

PRIORITY DATA

This application is a continuation of U.S. patent application Ser. No. 15/278,800, filed on Sep. 28, 2016, which claims priority to U.S. Provisional Patent App. No. 62/235,052, filed on Sep. 30, 2015, each of which is incorporated by reference herein.

FIELD OF THE INVENTION

The present invention generally relates to processes for preparing high-viscosity cellulosic compounds from lignocellulosic biomass.

BACKGROUND OF THE INVENTION

Biomass refining (or biorefining) has become more prevalent in industry. Cellulose fibers and sugars, hemicellulose sugars, lignin, syngas, and derivatives of these intermediates are being utilized for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Despite being the most available natural polymer on earth, it is only recently that cellulose has gained prominence as a nanostructured material, in the form of nanocrystalline cellulose (NCC), nanofibrillar cellulose (NFC), and bacterial cellulose (BC). Nanocellulose and microcellulose are being developed for use in a wide variety of applications such as polymer reinforcement, anti-microbial films, biodegradable food packaging, printing papers, pigments and inks, paper and board packaging, barrier films, adhesives, biocomposites, wound healing, pharmaceuticals and drug delivery, textiles, water-soluble polymers, construction materials, recyclable interior and structural components for the transportation industry, rheology modifiers, low-calorie food additives, cosmetics thickeners, pharmaceutical tablet binders, bioactive paper, pickering stabilizers for emulsion and particle stabilized foams, paint formulations, films for optical switching, and detergents.

Oil and natural gas are common fossil-based resources used for the production of transportation fuels, heat and power, materials, chemicals, adhesives, pharmaceuticals, polymers, fibers and other products. Since the first oil well drilled in 1859 and the introduction of the internal combustion engine, the United States has been a major producer and consumer of fossil resources.

In 2010, the U.S. produced over 2 billion barrels of oil and 26.8 trillion cubic feet of natural gas worth over $180 and $110 billion, respectively. A significant amount of this production can be attributed to advances in horizontal drilling and hydraulic fracturing. Previously unrecoverable deposits have been freed up ensuring access to decades of domestic natural gas and oil.

Oil and natural gas deposits are located all across the United States and the world. It is estimated that the total amount of technically recoverable natural gas resources worldwide is 22,600 trillion cubic feet of which shale gas is 6,622 trillion cubic feet or nearly 30% (*World Shale Gas Resources: An Initial Assessment of* 14 *Regions Outside the United States*, U.S. Department of Energy and Energy Information Administration, 2011). Wells are drilled hundreds of meters deep in order to gain access to the resources. Once drilled, new wells or old unproductive wells are hydraulically fractured to stimulate production.

Drilling fluids or muds are used during the initial well bore to cool the bit, lubricate the drill string, suspend and transport cuttings, control hydrostatic pressure and maintain stability. Drilling fluids are typically water-based or oil-based but can be pneumatic. Water or oil is the main ingredient in liquid drilling fluids. Barite, clay, polymers, thinners, surfactants, inorganic chemicals, bridging materials, lost circulation materials and specialized chemicals are also added to engineer drilling fluid properties.

Hydraulic fracturing was developed in the 1940s to increase productivity of oil and gas wells. Hydraulic fracturing creates and maintains cracks within oil and gas formations providing a clear path for oil and gas to flow. Fracturing can be performed in vertical and horizontal wells. During a fracturing operation, perforations are made through cement casing into the oil and gas formation using explosive charges. Fracturing fluids are injected into the well at high pressures to create new cracks while further expanding and elongating the cracks (*Hydraulic Fracturing: Unlocking America's Natural Gas Resources*, American Petroleum Institute, 2010).

Fracturing fluids are composed primarily of water (87-94%) and proppant such as sand (4-9%). Sand mixed with the fracturing fluids is used to prop open formation cracks and maintain a clear path for oil and natural gas. The remaining fracturing fluid (0.5-3%) is composed of chemicals that aid the fracturing process. Chemical additives are mixed into the drilling fluid depending on the well and formation properties. Chemicals are used to dissolve minerals, reduce friction, prevent scaling, maintain fluid properties (viscosity, pH, etc.), eliminate bacteria (biocide), suspend the sand, prevent precipitation of metal oxides, prevent corrosion, stabilize fluid, formation and wellbore, thicken fluid (gelling agent) and break down the gel (breaker).

Hydraulic fracturing fluid is made in a step-wise procedure and carefully engineered to accomplish the fracking process. In its most basic form, a gelling agent (typically gaur gum) is first added to water and hydrated. Next a breaker (oxidant or enzyme) is added which will break the gel bonds after being pumped into the well. A crosslinking agent such as borate is then added to the solution which immediately forms a viscous, gelled solution. The purpose of the gel is to suspend the proppant while being pumped into the well where it is wedged into formation fractures propping them apart.

Eventually the fracturing fluid must be removed from the well leaving the proppant in the fractures to maintain open channels for oil or gas to flow through. In order to pump the fracturing fluid out of the well and leave the proppant behind the viscous gel must be broken down to a viscosity less than 100 cP. Since the fracturing fluid is pumped into the well in stages, precise amounts of breaker are mixed with the fracturing fluid to break the entire gel solution simultaneously. Once the entire gel is broken the fracturing fluid is pumped back to the surface where it is stored in retention ponds or hauled away from the well for treatment and disposal.

What are needed in the art are methods and products that minimize environmental impact and costs of drilling, treating and hydraulic fracturing for oil and gas. Improved compositions are desired, including biomass-derived compositions. While cellulose-based materials have been generally recognized as possible components in drilling and fracturing fluids, heretofore there has not been an economical process to provide cellulose-based materials, with adjustable properties for different types of fluids and additives.

SUMMARY OF THE INVENTION

The present invention addresses the aforementioned needs in the art.

Some variations provide a process for producing a nanocellulose material, the process comprising:
- (a) providing a lignocellulosic biomass feedstock;
- (b) digesting the feedstock with a reaction solution including steam and/or hot water in a digestor under effective reaction conditions to produce a digested stream containing cellulose-rich solids, hemicellulose oligomers, and lignin;
- (c) optionally washing the cellulose-rich solids to remove at least a portion of the hemicellulose oligomers and/or at least a portion of the lignin from the cellulose-rich solids;
- (d) mechanically treating the cellulose-rich solids to form a nanocellulose material containing cellulose nanofibrils and/or cellulose nanocrystals; and
- (e) recovering the nanocellulose material.

The process may further include treatment of the cellulose-rich solids with one or more enzymes (e.g., cellulases) or with one or more acids, such as sulfur dioxide, sulfurous acid, lignosulfonic acid, acetic acid, formic acid, or combinations thereof. The process may further include treatment of the cellulose-rich solids with heat. In some embodiments, steps (b)-(d) do not employ any enzymes or externally added acids.

The nanocellulose material may include cellulose nanofibrils or a mixture of cellulose nanofibrils and cellulose nanocrystals. The nanocellulose material may also include lignin, including lignin particles less than 1 micron in diameter. The process may include bleaching the cellulose-rich solids and/or bleaching the nanocellulose material.

In some embodiments, the process further comprises recovering, fermenting, or further treating hemicellulosic sugars derived from the hemicellulose oligomers. For example, the hemicellulosic sugars may be fermented to a fermentation product, such as (but not limited to) ethanol.

In some embodiments, the process further comprises hydrolyzing a portion of the cellulose-rich solids into glucose, recovering the glucose, and optionally fermenting the glucose to a fermentation product, such as n-butanol or 1,4-butanediol.

The process may further include recovering, combusting, or further treating the lignin that is washed from the cellulose-rich solids. Some or all of the initial lignin (in the starting feedstock) may become part of the nanocellulose material, which will be at least partially hydrophobic due to the presence of the lignin.

In some embodiments, the process further comprises chemically converting the nanocellulose material to one or more nanocellulose derivatives. For example, nanocellulose derivatives may be selected from the group consisting of nanocellulose esters, nanocellulose ethers, nanocellulose ether esters, alkylated nanocellulose compounds, cross-linked nanocellulose compounds, acid-functionalized nanocellulose compounds, base-functionalized nanocellulose compounds, and combinations thereof.

In certain embodiments, step (d) includes disk refining followed by homogenization of the cellulose-rich solids. Step (d), or a portion thereof, may be conducted at a solids consistency of at least 10 wt %, such as at least 20 wt %.

The process includes, in some embodiments, exploding cellulose fibers contained in the cellulose-rich solids. The exploding of fibers may be achieved using steam explosion and/or rapid pressure reduction, for example. In certain embodiments, step (d) utilizes a blow-line refiner, optionally with pressure reduction.

Other variations of the invention provide a process for producing a biomass-derived rheology modifier from cellulosic biomass, the process comprising:
- (a) providing a feedstock comprising cellulosic biomass;
- (b) digesting the feedstock with a reaction solution including steam and/or hot water in a digestor under effective reaction conditions to produce a digested stream containing cellulose-rich solids, hemicellulose oligomers, and lignin;
- (c) refining the cellulose-rich solids in a first high-intensity refining unit, thereby generating refined cellulose solids;
- (d) washing the refined cellulose solids following step (c), and/or washing the digested stream prior to step (c) followed by the refining, thereby generating washed refined cellulose solids;
- (e) gelling the washed refined cellulose solids in a second high-intensity refining unit, thereby generating gelled cellulose solids; and
- (f) homogenizing the gelled cellulose solids in a high-shear homogenizer, thereby generating a biomass-derived rheology modifier containing cellulose nanofibrils, cellulose nanocrystals, or a mixture of cellulose nanofibrils and cellulose nanocrystals.

Optionally, the process further comprises wet or dry cleaning the feedstock prior to step (b). Optionally, whether or not the feedstock is cleaned, the process further comprises reducing size of the feedstock prior to step (b).

Step (b) may be conducted at a digestion temperature from about 140° C. to about 210° C. Step (b) may be conducted for a digestion time from about 5 minutes to about 45 minutes. Step (b) may be conducted at a liquid/solid weight ratio from about 2 to about 6.

The process may include a hot-blow or cold-blow pressure reduction of the digested stream, following step (b).

The first high-intensity refining unit may utilize disks or a conical plate, for example. In various embodiments, the first high-intensity refining unit transfers energy to the cellulose-rich solids in an amount from about 20 kW/ton to about 200 kW/ton (bone-dry basis).

Washing in step (d) may be conducted at a temperature from about 18° C. to about 95° C. In some embodiments, washing in step (d) utilizes a pressurized screw press.

The second high-intensity refining unit may utilize disks or a conical plate, for example. The first and second high-intensity refining units preferably have different patterns with different groove and dam dimensions. In various embodiments, the second high-intensity refining unit transfers energy to the washed refined cellulose solids in an amount from about 20 kW/ton to about 200 kW/ton (bone-dry basis).

In some embodiments, the high-shear homogenizer transfers a shear force equivalent to a shear force produced under a pressure from about 10,000 psig to about 25,000 psig.

In some embodiments, the washed refined cellulose solids are stored for a period of time prior to step (e). Step (e) may be conducted at a different location than steps (a)-(d). Also, step (f) may be conducted at a different location than steps (a)-(e).

Other variations of the invention provide a process for producing a biomass-derived rheology modifier from cellulosic biomass, the process comprising:
  (a) providing a pretreated feedstock comprising cellulose-rich solids;
  (b) refining the cellulose-rich solids in a first high-intensity refining unit, thereby generating refined cellulose solids;
  (c) optionally washing the refined cellulose solids following step (b), and/or optionally washing the digested stream prior to step (b) followed by the refining, thereby generating washed refined cellulose solids;
  (d) gelling the washed refined cellulose solids in a second high-intensity refining unit, thereby generating gelled cellulose solids; and
  (e) homogenizing the gelled cellulose solids in a high-shear homogenizer, thereby generating a biomass-derived rheology modifier containing cellulose nanofibrils.

In some embodiments, the pretreated feedstock is kraft pulp derived from wood or lignocellulosic biomass. In some embodiments, the pretreated feedstock is sulfite pulp derived from wood or lignocellulosic biomass. In some embodiments, the pretreated feedstock is soda pulp derived from wood or lignocellulosic biomass. In some embodiments, the pretreated feedstock is mechanical pulp derived from wood or lignocellulosic biomass. In some embodiments, the pretreated feedstock is thermomechanical pulp derived from wood or lignocellulosic biomass. In some embodiments, the pretreated feedstock is chemimechanical pulp derived from wood or lignocellulosic biomass.

In certain embodiments, the pretreated feedstock is obtained from fractionation of lignocellulosic biomass in the presence of water, an acid catalyst, and a solvent for lignin. In some embodiments, the pretreated feedstock may be AVAP® pulp derived from wood or lignocellulosic biomass. In certain embodiments, the pretreated feedstock is obtained from steam or hot-water extraction of lignocellulosic biomass. The pretreated feedstock may be GP3+® pulp derived from wood or lignocellulosic biomass.

Variations of the invention provide a water-based hydraulic fracturing fluid formulation or additive comprising (i) a nanocellulose material produced in accordance with a process as described or (ii) a biomass-derived rheology modifier produced in accordance with a process as described.

Variations of the invention provide an oil-based hydraulic fracturing fluid formulation or additive comprising (i) a nanocellulose material produced in accordance with the process as described or (ii) a biomass-derived rheology modifier produced in accordance with the process as described.

Variations of the invention provide a water-based drilling fluid formulation or additive comprising (i) a nanocellulose material produced in accordance with the process as described or (ii) a biomass-derived rheology modifier produced in accordance with the process as described.

Variations of the invention provide an oil-based drilling fluid formulation or additive comprising (i) a nanocellulose material produced in accordance with the process as described or (ii) a biomass-derived rheology modifier produced in accordance with the process as described.

Some variations provide a polymer-nanocellulose composite comprising (i) a nanocellulose material produced in accordance with the process as described or (ii) a biomass-derived rheology modifier produced in accordance with the process as described.

DETAILED DESCRIPTION OF EMBODIMENTS OF THE INVENTION

Figure 1A:
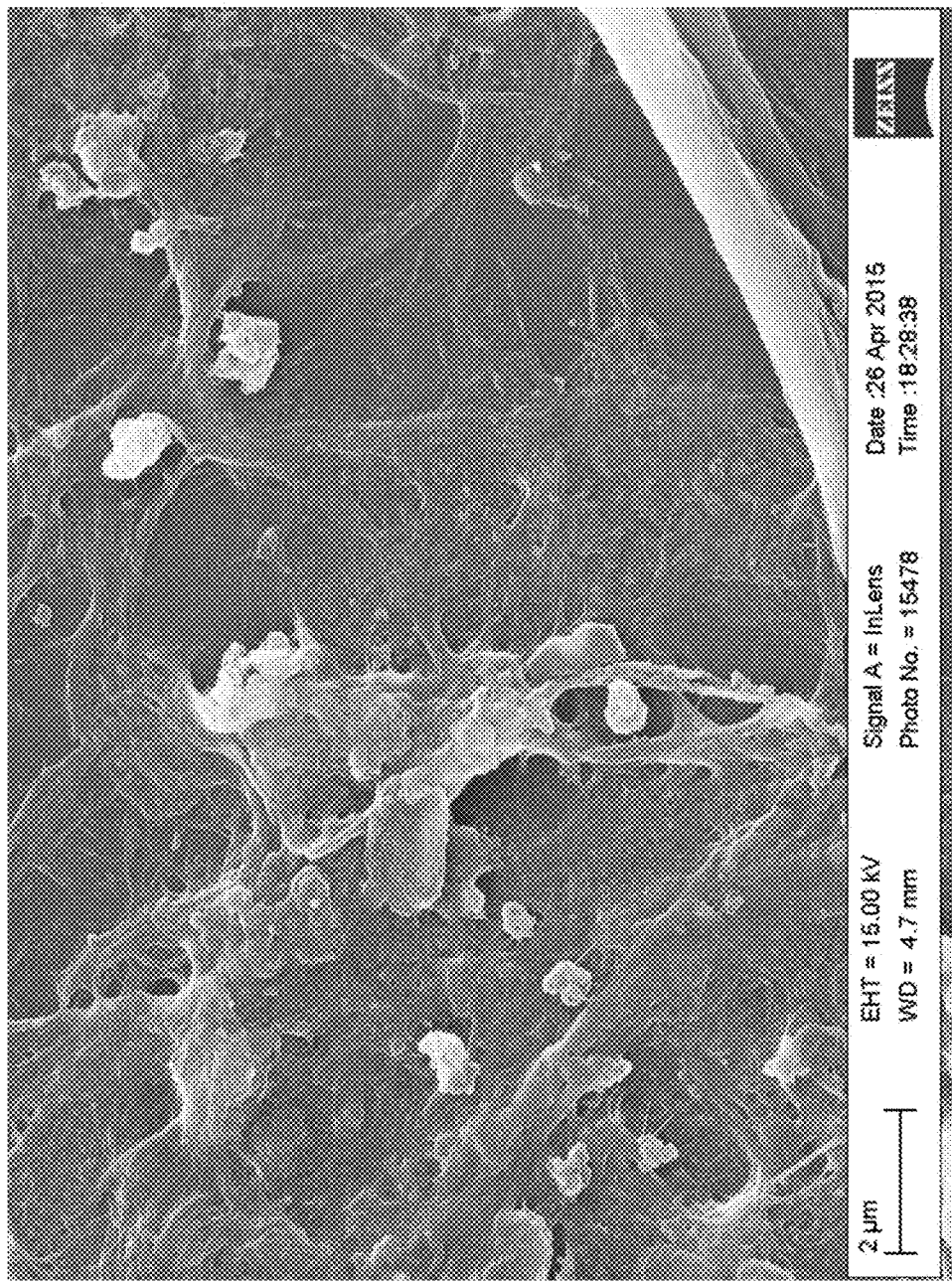
FIG. 1A is a SEM image of cellulose nanofibrils and cellulose nanocrystals produced in some embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Some variations are premised on the discovery of a surprisingly simple process for converting lignocellulosic biomass into fermentable sugars. Biomass may be subjected to a steam or hot-water soak to dissolved hemicelluloses, with or without acetic acid recycle. This step is followed by mechanical refining, such as in a hot-blow refiner, of the cellulose-rich (and lignin-rich) solids. The refined solids are then enzymatically hydrolyzed to generate sugars. A stripping step for removing fermentation inhibitors in the hydrolysate may be included.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only. In the drawings, dotted lines denote optional streams or units.

Some variations of the present invention are premised on relatively simple processes to generate high-viscosity compounds made from cellulosic biomass. The high-viscosity compounds will act as rheology modifiers when mixed in small proportions with different fluids, such as drilling fluids, paints, etc.

In hydraulic fracturing fluid formulations, particularly water-based formulations but also for oil-based formulations, these compositions may function as gelling agents. Easy mixing and handling allows for customization for each reservoir characteristics. Several properties of these rheology modifiers present strong advantages when compared to current available products on the market. Some of these properties are higher thermal stability, strong shear thinning, thixotropic qualities, and water solubility. Another important property of these new compounds is that they are biodegradable, and their production does not involve any chemicals other than biomass and water.

Some variations provide a process for producing a nanocellulose material, the process comprising:
  (a) providing a lignocellulosic biomass feedstock;
  (b) digesting the feedstock with a reaction solution including steam and/or hot water in a digestor under effective reaction conditions to produce a digested stream containing cellulose-rich solids, hemicellulose oligomers, and lignin;
  (c) optionally washing the cellulose-rich solids to remove at least a portion of the hemicellulose oligomers and/or at least a portion of the lignin from the cellulose-rich solids;
  (d) mechanically treating the cellulose-rich solids to form a nanocellulose material containing cellulose nanofibrils and/or cellulose nanocrystals; and
  (e) recovering the nanocellulose material.

The process may further include treatment of the cellulose-rich solids with one or more enzymes (e.g., cellulases) or with one or more acids, such as sulfur dioxide, sulfurous acid, lignosulfonic acid, acetic acid, formic acid, or combinations thereof. The process may further include treatment of the cellulose-rich solids with heat. In some embodiments, steps (b)-(d) do not employ any enzymes or externally added acids.

Figure 1B:
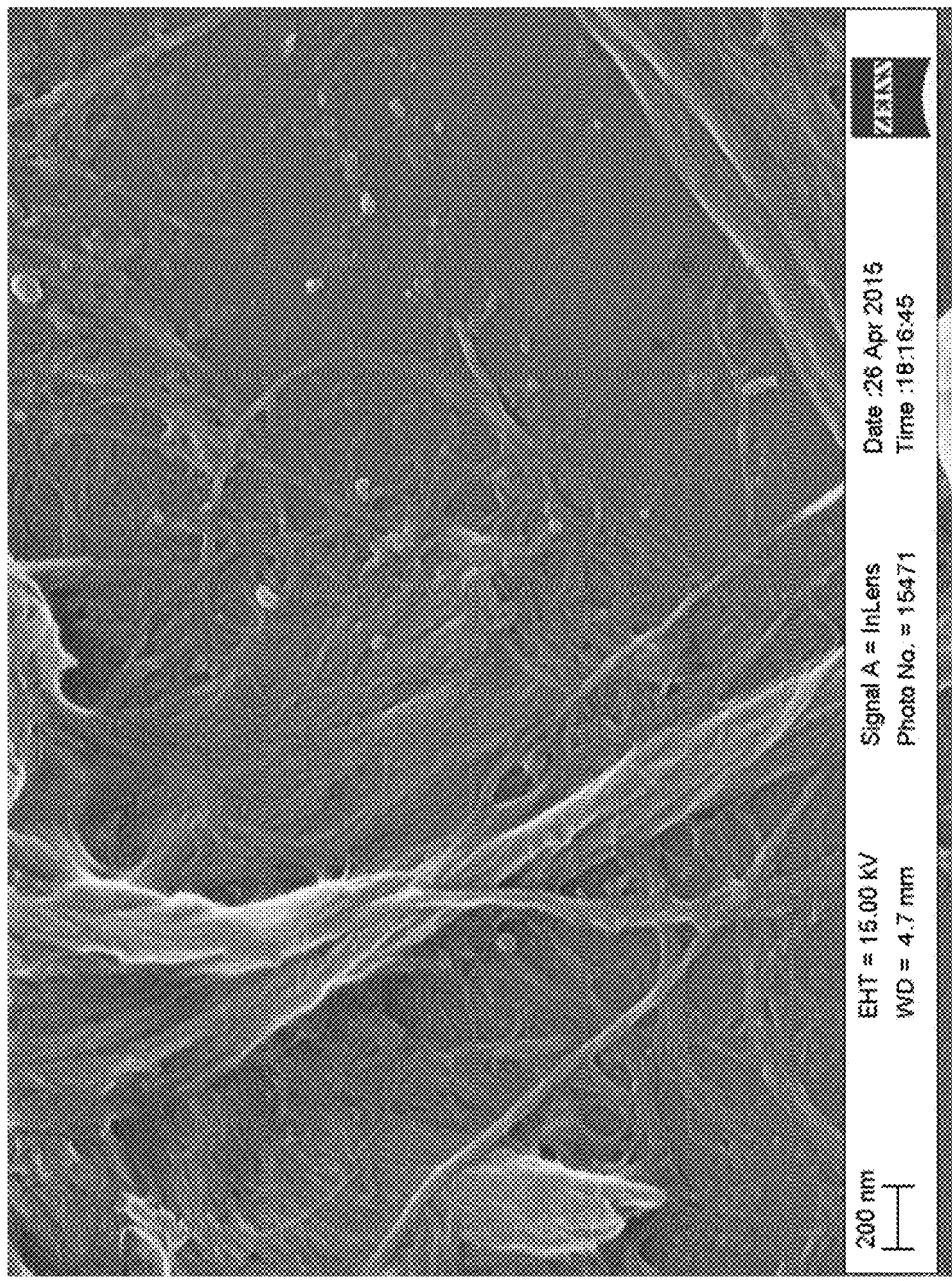
FIG. 1B is a SEM image of cellulose nanofibrils and cellulose nanocrystals produced in some embodiments.
Figure 1C:
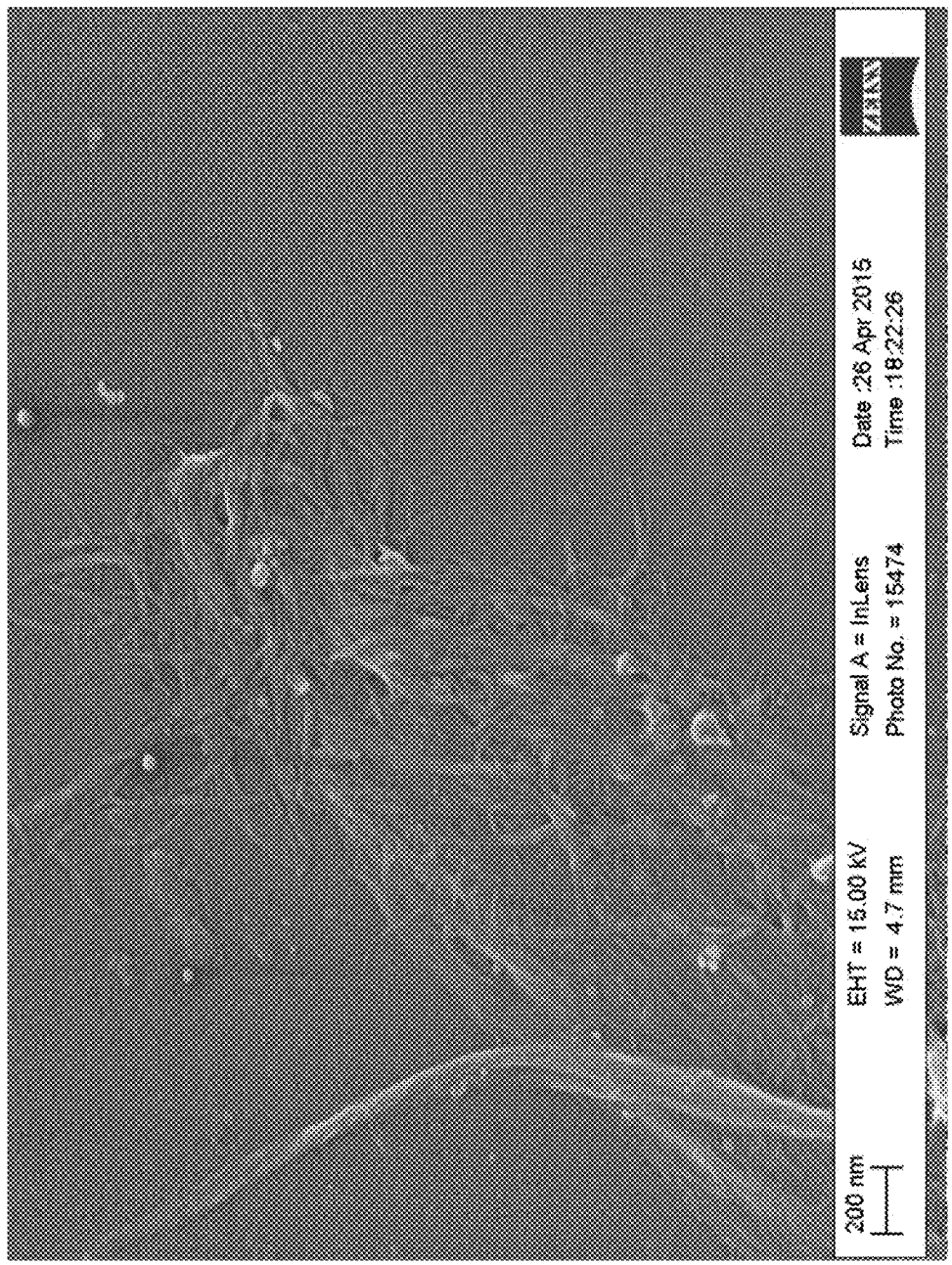
FIG. 1C is a SEM image of cellulose nanofibrils and cellulose nanocrystals produced in some embodiments.

The nanocellulose material may include cellulose nanofibrils or a mixture of cellulose nanofibrils and cellulose nanocrystals. FIGS. 1A-1C show SEM images of exemplary nanocellulose produced experimentally, by refining and homogenizing material produced from hot-water extraction of biomass. The nanocellulose material may also include lignin, including lignin particles less than 1 micron in diameter. The process may include bleaching the cellulose-rich solids and/or bleaching the nanocellulose material after it is produced.

In some embodiments, the process further comprises recovering, fermenting, or further treating hemicellulosic sugars derived from the hemicellulose oligomers. For example, the hemicellulosic sugars may be fermented to a fermentation product, such as (but not limited to) ethanol.

In some embodiments, the process further comprises hydrolyzing a portion of the cellulose-rich solids into glucose, recovering the glucose, and optionally fermenting the glucose to a fermentation product, such as n-butanol or 1,4-butanediol.

The process may further include recovering, combusting, or further treating the lignin that is washed from the cellulose-rich solids. Some or all of the initial lignin (in the starting feedstock) may become part of the nanocellulose material, which will be at least partially hydrophobic due to the presence of the lignin.

In some embodiments, the process further comprises chemically converting the nanocellulose material to one or more nanocellulose derivatives. For example, nanocellulose derivatives may be selected from the group consisting of nanocellulose esters, nanocellulose ethers, nanocellulose ether esters, alkylated nanocellulose compounds, cross-linked nanocellulose compounds, acid-functionalized nanocellulose compounds, base-functionalized nanocellulose compounds, and combinations thereof.

In certain embodiments, step (d) includes disk refining followed by homogenization of the cellulose-rich solids. Step (d), or a portion thereof, may be conducted at a solids consistency of at least 10 wt %, such as at least 20 wt %.

The process includes, in some embodiments, exploding cellulose fibers contained in the cellulose-rich solids. The exploding of fibers may be achieved using steam explosion and/or rapid pressure reduction, for example. In certain embodiments, step (d) utilizes a blow-line refiner, optionally with pressure reduction.

Figure 2:
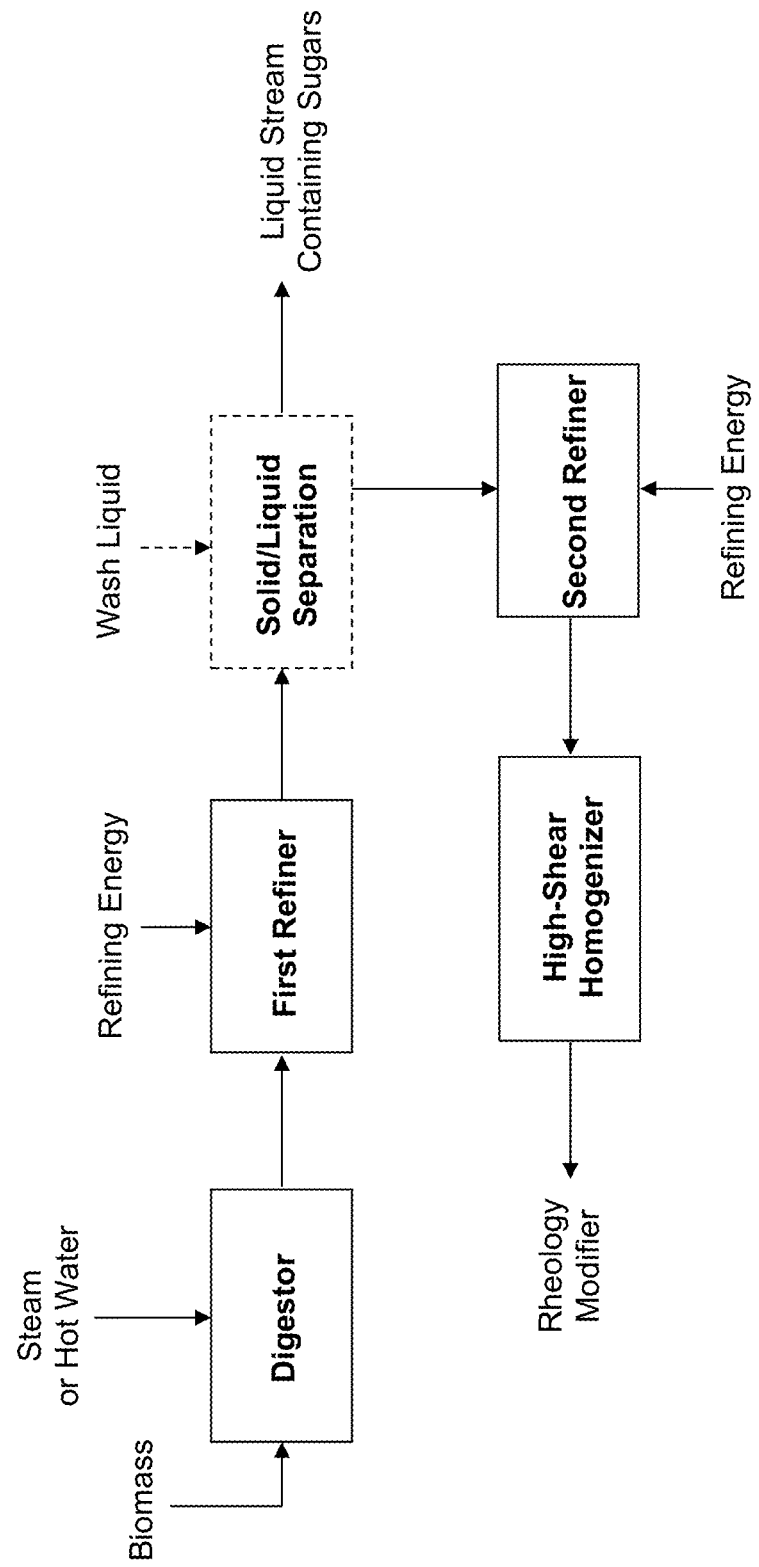
FIG. 2 is a simplified block-flow diagram depicting the process of some embodiments of the present invention.
Figure 3:
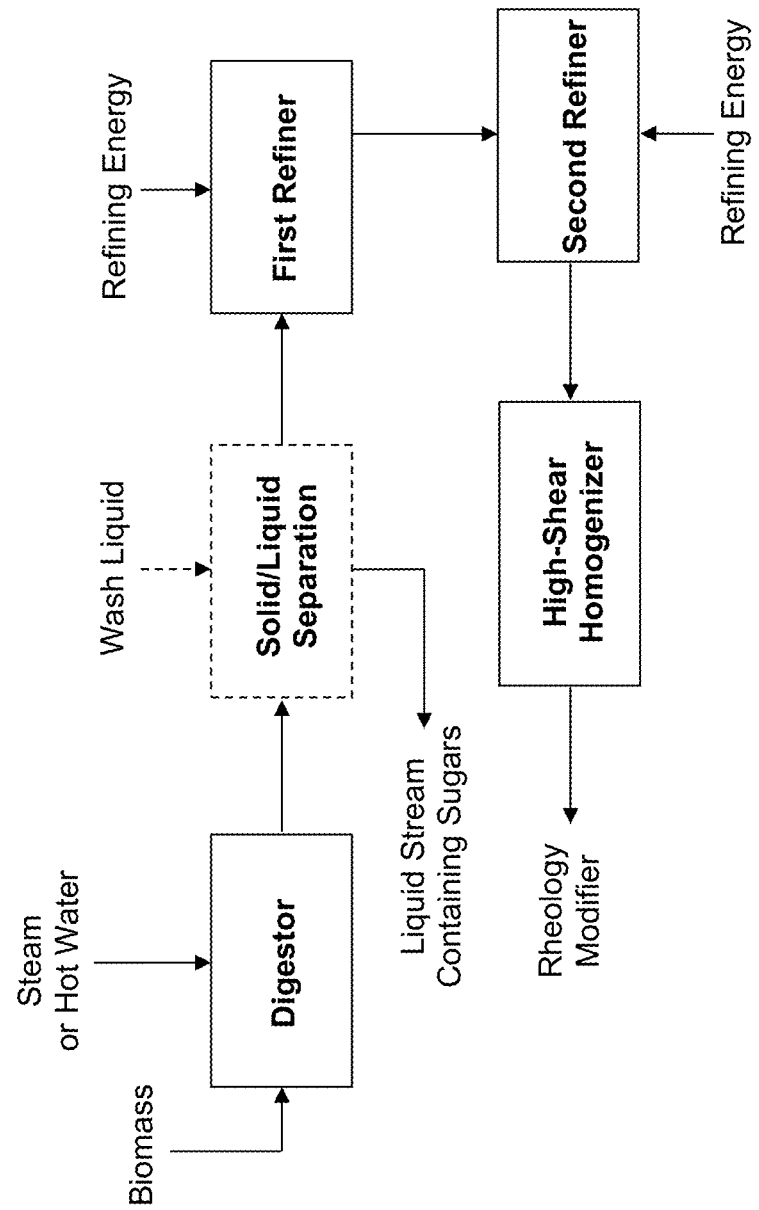
FIG. 3 is a simplified block-flow diagram depicting the process of some embodiments of the present invention.
Figure 4:
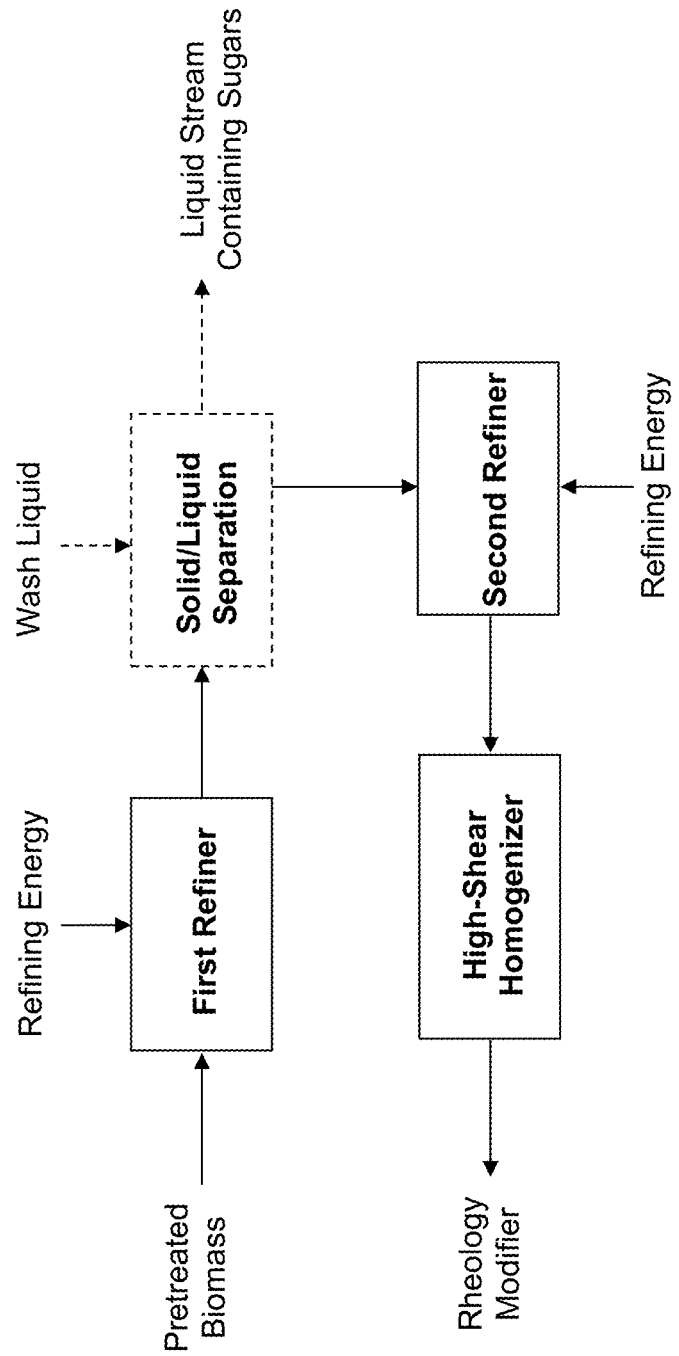
FIG. 4 is a simplified block-flow diagram depicting the process of various embodiments of the present invention.

FIGS. 2, 3, and 4 depict various process embodiments of this disclosure. Dotted lines denote optional streams or unit operations.

Some variations of the invention provide a process for producing a biomass-derived rheology modifier from cellulosic biomass, the process comprising:
  (a) providing a feedstock comprising cellulosic biomass;
  (b) digesting the feedstock with a reaction solution including steam and/or hot water in a digestor under effective reaction conditions to produce a digested stream containing cellulose-rich solids, hemicellulose oligomers, and lignin;

(c) refining the cellulose-rich solids in a first high-intensity refining unit, thereby generating refined cellulose solids;

(d) washing the refined cellulose solids following step (c), and/or washing the digested stream prior to step (c) followed by the refining, thereby generating washed refined cellulose solids;

(e) gelling the washed refined cellulose solids in a second high-intensity refining unit, thereby generating gelled cellulose solids; and (f) homogenizing the gelled cellulose solids in a high-shear homogenizer, thereby generating a biomass-derived rheology modifier containing cellulose nanofibrils, cellulose nanocrystals, or a mixture of cellulose nanofibrils and cellulose nanocrystals.

Optionally, the process further comprises wet or dry cleaning the feedstock prior to step (b). Optionally, whether or not the feedstock is cleaned, the process further comprises reducing size of the feedstock prior to step (b).

Step (b) may be conducted at a digestion temperature from about 140° C. to about 210° C. Step (b) may be conducted for a digestion time from about 5 minutes to about 45 minutes. Step (b) may be conducted at a liquid/solid weight ratio from about 2 to about 6.

The process may include a hot-blow or cold-blow pressure reduction of the digested stream, following step (b).

The first high-intensity refining unit may utilize disks or a conical plate, for example. In various embodiments, the first high-intensity refining unit transfers energy to the cellulose-rich solids in an amount from about 20 kW/ton to about 200 kW/ton (bone-dry basis).

Washing in step (d) may be conducted at a temperature from about 18° C. to about 95° ° C. In some embodiments, washing in step (d) utilizes a pressurized screw press.

The second high-intensity refining unit may utilize disks or a conical plate, for example. The first and second high-intensity refining units preferably have different patterns with different groove and dam dimensions. In various embodiments, the second high-intensity refining unit transfers energy to the washed refined cellulose solids in an amount from about 20 kW/ton to about 200 kW/ton (bone-dry basis).

In some embodiments, the high-shear homogenizer transfers a shear force equivalent to a shear force produced under a pressure from about 10,000 psig to about 25,000 psig.

In some embodiments, the washed refined cellulose solids are stored for a period of time prior to step (e). Step (e) may be conducted at a different location than steps (a)-(d). Also, step (f) may be conducted at a different location than steps (a)-(e).

Other variations of the invention provide a process for producing a biomass-derived rheology modifier from cellulosic biomass, the process comprising:

(a) providing a pretreated feedstock comprising cellulose-rich solids;

(b) refining the cellulose-rich solids in a first high-intensity refining unit, thereby generating refined cellulose solids;

(c) optionally washing the refined cellulose solids following step (b), and/or optionally washing the digested stream prior to step (b) followed by the refining, thereby generating washed refined cellulose solids;

(d) gelling the washed refined cellulose solids in a second high-intensity refining unit, thereby generating gelled cellulose solids; and (e) homogenizing the gelled cellulose solids in a high-shear homogenizer, thereby generating a biomass-derived rheology modifier containing cellulose nanofibrils.

In some embodiments, the pretreated feedstock is kraft pulp derived from wood or lignocellulosic biomass. In some embodiments, the pretreated feedstock is sulfite pulp derived from wood or lignocellulosic biomass. In some embodiments, the pretreated feedstock is soda pulp derived from wood or lignocellulosic biomass. In some embodiments, the pretreated feedstock is mechanical pulp derived from wood or lignocellulosic biomass. In some embodiments, the pretreated feedstock is thermomechanical pulp derived from wood or lignocellulosic biomass. In some embodiments, the pretreated feedstock is chemimechanical pulp derived from wood or lignocellulosic biomass.

In certain embodiments, the pretreated feedstock is obtained from fractionation of lignocellulosic biomass in the presence of water, an acid catalyst, and a solvent for lignin. In some embodiments, the pretreated feedstock may be AVAP® pulp derived from wood or lignocellulosic biomass. In certain embodiments, the pretreated feedstock is obtained from steam or hot-water extraction of lignocellulosic biomass. The pretreated feedstock may be GP3+® pulp derived from wood or lignocellulosic biomass.

Variations of the invention provide a water-based hydraulic fracturing fluid formulation or additive comprising (i) a nanocellulose material produced in accordance with a process as described or (ii) a biomass-derived rheology modifier produced in accordance with a process as described.

Variations of the invention provide an oil-based hydraulic fracturing fluid formulation or additive comprising (i) a nanocellulose material produced in accordance with the process as described or (ii) a biomass-derived rheology modifier produced in accordance with the process as described.

Variations of the invention provide a water-based drilling fluid formulation or additive comprising (i) a nanocellulose material produced in accordance with the process as described or (ii) a biomass-derived rheology modifier produced in accordance with the process as described.

Variations of the invention provide an oil-based drilling fluid formulation or additive comprising (i) a nanocellulose material produced in accordance with the process as described or (ii) a biomass-derived rheology modifier produced in accordance with the process as described.

Some variations provide a polymer-nanocellulose composite comprising (i) a nanocellulose material produced in accordance with the process as described or (ii) a biomass-derived rheology modifier produced in accordance with the process as described. Exemplary polymers include, but are not limited to, polylactide, poly(vinyl alcohol), polyethylene, polypropylene, etc.

Generally, the feedstock could be "residue biomass" with high cellulose content, typically between 25% and 75% on biomass weight, but not limited. In some cases, wood pulp may be used as the starting feedstock. Some embodiments employ the following steps:

1. After dry or/and wet cleaning, the biomass is reduced in size, typically using a set of knives, a shredder, a hammer mill, or a combination thereof.

2. Then the cleaned and size-reduced biomass is submitted to a "hot water treatment" (HWE) allowing the extraction of solubilized compounds. This thermal treatment is made continuously or in batch, subjecting the biomass with pressurized steam at a temperature between 140° C. and 210° C., generally between 175°

C. and 195° ° C. during a period of time between 5 minutes and 45 minutes, generally between 15 minutes and 30 minutes. The ratio of liquid (water and condensed steam) to solid (bone dry biomass) is between 2 to 1 to 6 to 1, such as between 3 to 1 to 3.5 to 1. This step could be referred to as "cooking," "digesting," "deconstruction," or "fractionation," for example.
3. Following there may be a "blow" (i.e. pressure reduction) which could be either gradual pressure reduction that could be referred as a "cold blow." If it is a sudden pressure reduction, this may be referred to as a "hot blow".
4. Next there is a stage of additional size reduction with the purpose of increasing the specific surface of the fiber by mechanical fiber cutting using a "high intensity pulp refiner" which could include a conical plate or disks. During this stage, there is a need for energy transfer to the pulp between 20 kw/ton BD and 200 kw/ton BD, preferably between 75 kw/ton BD and 150 kw/ton BD.
5. A pulp washing operation is optionally inserted either between the blow stage and the high-intensity refiner or following the high-intensity pulp refiner. The pulp washing is to separate the pulp (the solid fraction) and the steam-water solubilized product during the thermal treatment, i.e. the liquid fraction. This could be achieved in a batch process or in a continuous operation. In either case, the pulp is further washed with water. Washing water could be at a temperature between 18° C. and 95° C., preferably between 70° C. and 80° C., for example.
6. Following the optional water wash, which could be either countercurrent or cocurrent, the pulp may be either directed to the high-intensity pulp refiner or to a storage bin. Countercurrent continuous pulp washing preferably will be made immediately after the hot blow, using one or more of several commercially available solid-liquid separation systems, such as a pressurized screw press.
7. Next, the pulp is sent to a second disk refiner, to strongly transform the defibrillation of the pulp to a gel-type product generated by gelation. During this stage, there is a need for energy transfer to the pulp between 20 kw/ton BD and 200 kw/ton BD, preferably between 75 kw/ton BD and 150 kw/ton BD. The configuration of the plates for the first refiner ("high-intensity pulp refiner") and the second one ("second disk refiner") have different patterns with different groove and dam dimensions ratios.
8. Next the gel-type product is sent to a unit operation containing a high-shear homogenizer, where high-intensity shear is applied similar to an equivalent shear produced under 10,000 psig and 25,000 psig.

In some embodiments, this process creates high-viscosity compounds with size between 1 micron and 100 microns, such as between 15 micron and 50 microns. These new compounds produced without any chemicals (other than biomass and water) may be used as rheology modifiers and, being based on cellulose, are fully biodegradable.

The process presents several advantages. The design allows the process to be fully integrated in one line from the startup with the biomass through production of the high-viscosity compounds. Or the process could be separated in several modules which could be located at different geographical sites.

The biomass feedstock may be selected from hardwoods, softwoods, forest residues, agricultural residues (such as sugarcane bagasse), industrial wastes, consumer wastes, or combinations thereof. In any of these processes, the feedstock may include sucrose. In some embodiments with sucrose present in the feedstock, a majority of the sucrose is recovered as part of the fermentable sugars.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse, energy cane bagasse, sugarcane straw, or energy cane straw.

In some embodiments, the process further comprises wet or dry cleaning the feedstock prior to step (b). In some embodiments, the process further comprises reducing size of the feedstock prior to step (b). The process may include size reduction, hot-water soaking, dewatering, steaming, or other operations, upstream of the digestor.

Step (b) may be conducted at a digestion temperature from about 140° ° C. to about 210° C., such as from about 175° C. to about 195° C. Step (b) may be conducted for a digestion time from about 5 minutes to about 45 minutes, such as from about 15 minutes to about 30 minutes. Step (b) may be conducted at a liquid/solid weight ratio from about 2 to about 6, such as about 3, 3.5, 4, 4.5, or 5.

In some embodiments, the reaction solution comprises steam in saturated, superheated, or supersaturated form. In some embodiments, the reaction solution comprises hot water.

The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The solid-phase residence time for the digestor (pressurized extraction vessel) may vary from about 2 minutes to about 4 hours, such as about 5 minutes to about 1 hour. In certain embodiments, the digestor residence time is controlled to be about 5 to 15 minutes, such as 5, 6, 7, 8, 9, 10, 11, 12, 13, 14 or 15 minutes. The liquid-phase residence time for the digestor may vary from about 2 minutes to about 4 hours, such as about 5 minutes to about 1 hour. The vapor-phase residence time for the digestor may vary from about 1 minute to about 2 hours, for example, such as about 3 minutes to about 30 minutes. The solid-phase, liquid-phase, and vapor-phase residence times may all be about the same, or they may be independently controlled according to reactor-engineering principles (e.g., recycling and internal recirculation strategies).

In some embodiments, the process further comprises a hot-blow pressure reduction of the digested stream, following step (b). Alternatively, a cold-blow pressure reduction of the digested stream, following step (b), may be employed.

To reduce pressure, a blow tank may be situated between the digestor and the refining unit. In some embodiments, vapor is separated from the blow tank, and heat is recovered from at least some of the vapor. Optionally, at least some of the vapor is compressed and returned to the digestor, and/or at least some of the vapor is purged from the process. Note that "blow tank" should be broadly construed to include not only a tank but any other apparatus or equipment capable of allowing a pressure reduction in the process stream. Thus a blow tank (or blow means) may be a tank, vessel, section of pipe, valve, separation device, or other unit.

Each mechanical refiner may be selected from the group consisting of a hot-blow refiner, a hot-stock refiner, a disk refiner, a conical refiner, a cylindrical refiner, an in-line defibrator, a homogenizer, and combinations thereof. Mechanically treating (refining) may employ one or more known techniques such as, but by no means limited to, milling, grinding, beating, sonicating, or any other means to reduce cellulose particle size. Such refiners are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992.

The refining may be conducted at a wide range of solids concentrations (consistency), including from about 2% to about 50% consistency, such as about 3%, 4%, 5%, 6%, 7%, 8%, 9%, 10%, 11%, 12%, 15%, 20%, 30%, 35%, or 40% consistency.

Each mechanical refiner may be configured to transfer from about 20 to about 200 kW/ton (i.e., kW refining power per ton fiber, based on the solid phase that is converted to the refined stream). In certain embodiments, the mechanical refiner is configured to transfer from about 75 to about 150 KW refining power per ton fiber. For example, a mechanical refiner with plates may be adjusted by changing the plate type, gap, speed, etc. to achieve these power inputs.

The extent of mechanical treatment may be monitored during the process by any of several means. Certain optical instruments can provide continuous data relating to the fiber length distributions and % fines, either of which may be used to define endpoints for the mechanical treatment step. The time, temperature, and pressure may vary during mechanical treatment. For example, in some embodiments, sonication for a time from about 5 minutes to 2 hours, at ambient temperature and pressure, may be utilized.

In some embodiments, a portion of the cellulose-rich solids is converted to fibrillated and/or gelled while the remainder of the cellulose-rich solids is not fibrillated and/or gelled. In various embodiments, about 10%, 20%, 30%, 40%, 50%, 60%, 70%, 80%, 90%, 95%, 99%, or substantially all of the cellulose-rich solids are fibrillated and/or gelled.

The first high-intensity refining unit may utilize disks or a conical plate, for example. In some embodiments, the first high-intensity refining unit transfers energy to the cellulose-rich solids in an amount from about 20 kW/ton to about 200 kW/ton (bone-dry basis), such as from about 75 kW/ton to about 150 kW/ton (bone-dry basis).

In some embodiments, washing in step (d) is conducted at a temperature from about 18° C. to about 95° C., such as from about 70° C. to about 80° C. Washing in step (d) may utilize a pressurized screw press.

In some embodiments, the second high-intensity refining unit utilizes disks or a conical plate. The first and second high-intensity refining units preferably have different patterns with different groove and dam dimensions. In some embodiments, the second high-intensity refining unit transfers energy to the washed refined cellulose solids in an amount from about 20 kW/ton to about 200 kW/ton (bone-dry basis), such as from about 75 kW/ton to about 150 kW/ton (bone-dry basis).

In some embodiments, the high-shear homogenizer (or other unit operation capable of imparting shear) transfers a shear force equivalent to a shear force produced under a pressure from about 1,000 psig to about 50,000 psig, such as about 10,000 psig to about 25,000 psig.

The washed refined cellulose solids may be stored for a period of time prior to step (e), which may be conducted at a different location than steps (a)-(d). In some embodiments, not step (f) is conducted at a different location than steps (a)-(e).

In some embodiments, the biomass-derived rheology modifier may be characterized by a particle size (e.g., fiber or fibril length or effective length) from about 1 microns to about 100 microns, such as from about 1 micron to about 50 microns. In certain embodiments, a majority (such as about 50%, 60%, 70%, 80%, 90%, or 95%) of the particles are in the size range of 10-15 microns. The biomass-derived rheology modifier may include particles smaller than 5 microns, such as 4, 3, 2, 1 micron or less (i.e. nanoparticles). The width of the particles may be less than 1 micron. Particles larger than 100 microns, such as 150, 200, 250, 300, 400, 500 microns or greater, may be present.

In some embodiments, the biomass-derived rheology modifier may be characterized by a particle size (e.g., length or effective length) less than about 10 microns, such as about 9, 8, 7, 6, 5, 4, 3, 2, 1 micron or less. In certain embodiments, the nanocellulose particle length is about 900, 800, 700, 600, 500, 400, 300, 200, 100 nm or less. In these or other embodiments (including lengths in excess of 1 micron), the nanocellulose particle diameter may be from about 3 nm to about 1000 nm, such as from about 5 nm to about 500 nm, or about 10 nm to about 200 nm or about 5, 10, 15, 20, 25, 30, 40, 50, 60, 70, 80, 90, 100, 150, 200, 250, 300, 350, 400, or 450 nm. In some of these embodiments, the nanoparticles (or a portion of them) may be characterized as nanocrystals.

The rheology modifier compounds are primarily cellulose-based polymers, with some microcrystalline shape like nanocellulose including some of the initial biomass lignin in the structure. In some embodiments, the compound properties are predominantly hydrophilic, allowing a strong stability of water-based drilling fluid and water-based fracking fluids. In some embodiments with lignin content and suitable high-intensity refining, the compounds are hydrophobic, moderately hydrophobic, or a combination of hydrophilic and hydrophobic.

The present disclosure provides a water-based hydraulic fracturing fluid formulation or additive comprising a biomass-derived rheology modifier produced in accordance with the processes described herein.

The present disclosure provides an oil-based hydraulic fracturing fluid formulation or additive comprising a biomass-derived rheology modifier produced in accordance with the processes described herein.

The present disclosure provides a water-based drilling fluid formulation or additive comprising a biomass-derived rheology modifier produced in accordance with the processes described herein.

The present disclosure provides an oil-based drilling fluid formulation or additive comprising a biomass-derived rheology modifier produced in accordance with the processes described herein.

The process may further include removal of one or more fermentation inhibitors (such as acetic acid or furfural) by stripping. This stripping may be conducted by treating the hydrolyzed cellulose stream, prior to fermentation. Alternatively, or additionally, the stripping may be conducted on a stream following digestion, such as in the blow line.

The process in some embodiments further comprises a step of fermenting the fermentable sugars, contained in the liquid phase derived from the initial digestion, to a dilute fermentation product. The process further may comprise concentration and purification of the fermentation product. The fermentation product may be selected from ethanol, n-butanol, 1,4-butanediol, succinic acid, lactic acid, or combinations thereof, for example. Also, a solid stream containing lignin may be removed, either prior to fermentation or downstream of fermentation.

A step may include conditioning of hydrolysate to remove some or most of the volatile acids and other fermentation inhibitors. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) to assist in the removal of hemicelluloses or minerals from the biomass. This recycle of organic acids, such as acetic acid, may be optimized along with process conditions that may vary depending on the amount recycled, to improve the cooking effectiveness.

A step may include recovering fermentable sugars, which may be stored, transported, or processed. A step may include fermenting the fermentable sugars to a co-product (the primary product being rheology modifiers).

A step may include preparing solid residuals (containing lignin) for combustion. This step may include refining, milling, fluidizing, compacting, and/or pelletizing the dried, extracted biomass. The solid residuals may be fed to a boiler in the form of fine powder, loose fiber, pellets, briquettes, extrudates, or any other suitable form. Using known equipment, solid residuals may be extruded through a pressurized chamber to form uniformly sized pellets or briquettes.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning, after concentration of the distillation bottoms.

Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

The process may be continuous, semi-continuous, or batch. When continuous or semi-continuous, the stripping column may be operated countercurrently, cocurrently, or a combination thereof.

The process may further comprise bleaching the cellulose-rich solids prior to a refining step and/or as part of refining. Alternatively, or additionally, the process may further comprise bleaching the refined material, the gelled material, or the homogenized material. Any known bleaching technology or sequence may be employed, including enzymatic bleaching.

Rheology modifiers as provided herein may be incorporated into drilling fluids, drilling fluid additives, fracturing fluids, and fracturing fluid additives. The rheology modifiers may be present in a wide variety of concentrations, such as from about 0.001 wt % to about 10 wt % or higher, e.g. about 0.01 wt %, 0.05 wt %, 0.1 wt %, 0.5 wt %, 1 wt %, or 2 wt %.

The invention, in some variations, is related to a group of cellulosic compounds which could be used in different applications. One of the applications is to use them as product enhancers of drilling fluids. The rheology modifiers may serve one or more functions in drilling fluids. For example, the rheology modifier may serve as a gelling agent to increase viscosity, or a viscosifier in general. The rheology modifier may serve as a friction reducer. Also, rheology modifiers may be a drilling polymer, displacing other polymers or adding to them.

Drilling fluids are fluids used in drilling in the natural gas and oil industries, as well as other industries that use large drilling equipment. The drilling fluids are used to lubricate, provide hydrostatic pressure, keep the drill cool, and keep the hole as clean as possible of drill cuttings. Rheology modifiers provided herein are suitable as additives to these drilling fluids.

In some embodiments, these rheology modifier compositions provide one or more of the following functions or advantages:

Polymeric viscosifiers
Predictable shear thinning
Rheology modifiers to enhance drilling efficiency
Provide increased viscosity of the fracturing fluid
Provide lower friction loss which will increase the rate of penetration by reducing the injection pressure hence enhance reducing fracking time
Shear thinning
Gelling agents
Linear gels
Stable crosslinked products
Friction reducers
Provide improved performance of proppant transport, and for well cleanup
Biodegradable
Produced from biomass In some embodiments, enzymes can be used as a "breaker" with the compositions, to break down rheology modifiers after some period of time or under certain conditions (e.g., temperature or pH).

In some embodiments, lignosulfonates are incorporated for enhanced lubricity in drilling applications. Also, the ability of lignosulfonates to reduce the viscosity of mineral slurries can be beneficial in oil drilling muds.

In some embodiments, native lignin or non-sulfonated lignin, or non-sulfonated lignin derivatives, are incorporated into the compositions.

Some embodiments provide a drilling fluid additive comprising rheology modifiers.

Some embodiments provide a drilling fluid additive comprising rheology modifiers, wherein the additive further comprises lignosulfonates.

Some embodiments provide a drilling fluid additive comprising rheology modifiers, wherein the additive further comprises non-sulfonated lignin.

Some embodiments provide a drilling fluid additive comprising rheology modifiers, wherein the additive further comprises a crosslinking agent.

Some embodiments provide a drilling fluid additive comprising crosslinked rheology modifiers and lignosulfonates.

Some embodiments provide drilling fluids comprising the drilling fluid additives as disclosed. The drilling fluid may be a water-based drilling fluid, an oil-based drilling fluid, or a hybrid water-based/oil-based drilling fluid.

In various embodiments, the drilling fluid further comprises one or more of a biomass-derived weighting material, a biomass-derived filtration-control agent, a biomass-derived rheology-control agent, a biomass-derived pH-control agent, a biomass-derived lost-circulation material, a biomass-derived surface-activity modifier, a biomass-derived lubricant, and a biomass-derived flocculant, and/or a biomass-derived stabilizer.

In some variations, the invention provides a method of using a drilling fluid additive, the method comprising combining a drilling fluid additive as disclosed into a base fluid to generate a drilling fluid. In some variations, the invention provides a method comprising introducing a disclosed drilling fluid additive directly or indirectly into a geological formation.

In some variations, a method of drilling includes introducing a drilling fluid additive directly or indirectly into a geological formation, wherein the drilling fluid additive includes an enzyme for degelling under effective conditions. In related variations, a method of drilling includes introducing a drilling fluid additive directly or indirectly into a geological formation, and then later introducing an enzyme for degelling under effective conditions.

Some variations provide a process for producing a drilling fluid additive, the process comprising refining biomass under effective pretreatment conditions and refining conditions to generate a drilling fluid additive as disclosed. In some embodiments, the effective pretreatment conditions include the generation of lignosulfonic acids. Optionally, at least a portion of the lignosulfonic acids are not removed and remain present in the drilling fluid additive. In certain embodiments, the drilling fluid additive comprises a liquid slurry derived from the process. For example, the slurry may contain rheology modifiers derived from the biomass as well as water and pretreatment chemicals (such as acids, solvents, etc.).

Another application of these compositions is to use them as product enhancers of hydraulic fracturing fluids. Improvement in this purpose are particularly due to their impact in friction reduction, in improved pumping of proppants at a higher rate, at reduced pressure and predictable viscosity at high temperatures. Additionally, these products are fully biodegradable; they are produced from biomass, and are less susceptible to biofouling as could be other products like galactomannan derivatives.

Rheology modifiers may be crosslinked for robust gelling in fracking fluids. In some embodiments, crosslinking of rheology modifiers gives a stronger gel with more hydration.

Biomass-derived ash (from the biomass structure) or sand (from washing) may be used as a proppant, to displace mined silica.

The present invention, in other variations, provides fracturing fluid additives.

Some embodiments provide a fracturing fluid additive comprising rheology modifiers.

Some embodiments provide a fracturing fluid additive comprising rheology modifiers, wherein the additive further comprises lignosulfonates.

Some embodiments provide a fracturing fluid additive comprising rheology modifiers, wherein the additive further comprises non-sulfonated lignin.

Some embodiments provide a fracturing fluid additive comprising rheology modifiers, wherein the additive further comprises a crosslinking agent.

Some embodiments provide a fracturing fluid additive comprising crosslinked rheology modifiers and lignosulfonates.

Some embodiments provide a fracturing fluid comprising the fracturing fluid additive as disclosed. The fracturing fluid may be a water-based fracturing fluid, an oil-based fracturing fluid, or a hybrid water-based/oil-based fracturing fluid.

The fracturing fluid may further include, in addition to a disclosed fracturing fluid additive, one or more of a biomass-derived acid (such as acetic acid, formic acid, levulinic acid, and/or lignosulfonic acid), a biomass-derived corrosion inhibitor (such as lignin or a lignin derivative), a biomass-derived friction reducer (such as lignosulfonate or a lignosulfonate derivative), a biomass-derived clay-control agent, a biomass-derived crosslinking agent, a biomass-derived scale inhibitor, a biomass-derived breaker, a biomass-derived iron-control agent, a biomass-derived biocide (e.g., biomass hydrolysate), and/or a biorefinery-derived source of recycled or recovered water. Typically, the fracturing fluid carries, includes, or is intended to be combined with a proppant, which may be a biomass-derived proppant (such as ash contained in the structure of biomass and/or sand, ash, or dirt collected with biomass).

Some variations of the invention provide a method of using a fracturing fluid additive, the method comprising combining a disclosed fracturing fluid additive into a base fluid to generate a fracturing fluid. Some methods include introducing a fracturing fluid additive directly or indirectly into a geological formation.

In some variations, a process for producing a fracturing fluid additive comprises refining biomass under effective pretreatment conditions and refining conditions to generate a fracturing fluid additive as disclosed. In some embodiments, the pretreatment conditions include the generation of lignosulfonic acids, which optionally are not entirely removed and are present in the fracturing fluid additive. In some embodiments, the fracturing fluid additive comprises a liquid slurry derived from the process. For example, the slurry may contain rheology modifiers derived from the biomass as well as water and pretreatment chemicals (e.g., solvents, acids, bases, and so on).

The rheology modifiers of some embodiments are characterized by an average cellulose degree of polymerization from about 100 to about 2000, such as from about 400 to about 1200 or from about 500 to about 800. In certain embodiments, the rheology modifiers are free of enzymes.

The present disclosure, while directed to rheology modifiers for use as additives and various compositions, is not limited to rheology modifiers. The material produced by the multiple refining steps (following biomass pretreatment) as disclosed, may be used in a wide variety of applications. For example, the rheology modifier may be incorporated into product selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

Some embodiments provide products with applications for sensors, catalysts, antimicrobial materials, current carrying and energy storage capabilities. Cellulose crystals have the capacity to assist in the synthesis of metallic and semiconducting chains.

Some embodiments provide composites containing refined cellulose and a carbon-containing material, such as (but not limited to) lignin, graphite, graphene, or carbon aerogels.

Cellulose crystals may be coupled with the stabilizing properties of surfactants and exploited for the fabrication of architectures of various semiconducting materials.

The reactive surface of —OH side groups in refined cellulose facilitates grafting chemical species to achieve different surface properties. Surface functionalization allows the tailoring of particle surface chemistry to facilitate self-assembly, controlled dispersion within a wide range of matrix polymers, and control of both the particle-particle and particle-matrix bond strength. Composites may be transparent, have tensile strengths greater than cast iron, and have very low coefficient of thermal expansion. Potential applications include, but are not limited to, barrier films, antimicrobial films, transparent films, flexible displays, reinforcing fillers for polymers, biomedical implants, pharmaceuticals, drug delivery, fibers and textiles, templates for electronic components, separation membranes, batteries, supercapacitors, electroactive polymers, and many others.

Other applications suitable to the present invention include reinforced polymers, adhesives, high-strength spun fibers and textiles, advanced composite materials, films for barrier and other properties, additives for coatings, paints, lacquers, adhesives, switchable optical devices, pharmaceuticals and drug delivery systems, bone replacement and tooth repair, improved paper, packaging and building products, additives for foods and cosmetics, catalysts, and hydrogels.

Aerospace and transportation composites may benefit from these rheology modifiers. Automotive applications include cellulose composites with polypropylene, polyamide (e.g. Nylons), or polyesters (e.g. PBT).

Rheology modifiers provided herein may be suitable as strength-enhancing additives for renewable and biodegradable composites. The cellulosic fibrillar structures may function as a binder between two organic phases for improved fracture toughness and prevention of crack formation for application in packaging, construction materials, appliances, and renewable fibers.

Rheology modifiers provided herein are may be as transparent and dimensional stable strength-enhancing additives and substrates for application in flexible displays, flexible circuits, printable electronics, and flexible solar panels. Cellulose is incorporated into the substrate-sheets are formed by vacuum filtration, dried under pressure and calandered, for example. In a sheet structure, cellulose acts as a glue between the filler aggregates. The formed calandered sheets are smooth and flexible.

Rheology modifiers provided herein may be suitable for composite and cement additives allowing for crack reduction and increased toughness and strength. Foamed, cellular cellulose-concrete hybrid materials allow for lightweight structures with increased crack reduction and strength.

Strength enhancement with cellulose increases both the binding area and binding strength for application in high strength, high bulk, high filler content paper and board with enhanced moisture and oxygen barrier properties. The pulp and paper industry in particular may benefit from rheology modifiers provided herein.

Porous cellulose may be used for cellular bioplastics, insulation and plastics and bioactive membranes and filters. Highly porous cellulose materials are generally of high interest in the manufacturing of filtration media as well as for biomedical applications, e.g., in dialysis membranes.

Rheology modifiers provided herein may be suitable as additives to improve the durability of paint, protecting paints and varnishes from attrition caused by UV radiation.

Rheology modifiers provided herein are suitable as thickening agents in food and cosmetics products. Rheology modifiers can be used as a thixotropic, biodegradable, dimensionally stable thickener (stable against temperature and salt addition). Rheology modifiers materials provided herein may be suitable as a Pickering stabilizer for emulsions and particle stabilized foam.

The large surface area of these rheology modifiers in combination with their biodegradability makes them attractive materials for highly porous, mechanically stable aerogels.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing a nanocellulose material, said process comprising:
    (a) providing a lignocellulosic biomass feedstock;
    (b) digesting said feedstock with a reaction solution consisting essentially of steam and/or hot water in a digestor under effective reaction conditions to produce a digested stream containing cellulose-rich solids, hemicellulose oligomers, and lignin, wherein said effective reaction conditions include a digestion temperature selected from above 140° ° C. to 210° C.;
    (c) optionally washing said cellulose-rich solids to remove at least a portion of said hemicellulose oligomers and at least a portion but not all of said lignin from said cellulose-rich solids;
    (d) mechanically treating said cellulose-rich solids to form a nanocellulose material containing cellulose nanofibrils and/or cellulose nanocrystals, wherein said mechanically treating utilizes disk refining followed by homogenization of said cellulose-rich solids, wherein step (d) utilizes a mechanical-treatment power of about 20 to 200 kW/ton of solids; and
    (e) recovering said nanocellulose material, wherein said nanocellulose material is hydrophobic due to the presence of lignin, and wherein said nanocellulose material is characterized by (i) an average particle effective diameter from about 5 nanometers to about 500 nanometers and (ii) an average particle effective length from about 100 nanometers to about 1000 nanometers, and wherein process steps (a), (b), (c), (d), and (e) do not employ any enzymes, externally added acids, or combinations thereof.

2. The process of claim 1, wherein step (d) is conducted at a solids consistency of at least 10 wt %.

3. The process of claim 1, said process further comprising exploding cellulose fibers contained in said cellulose-rich solids.

4. The process of claim 1, wherein step (d) utilizes a blow-line refiner, optionally with pressure reduction.

5. The process of claim 1, wherein step (c) is conducted.

6. The process of claim 1, said process further comprising bleaching said cellulose-rich solids and/or said nanocellulose material.

7. The process of claim 1, wherein said nanocellulose material comprises said cellulose nanofibrils.

8. The process of claim 1, wherein said nanocellulose material comprises a mixture of said cellulose nanofibrils and said cellulose nanocrystals.

9. The process of claim 1, said process further comprising recovering, fermenting, or further treating hemicellulosic sugars derived from said hemicellulose oligomers.

10. The process of claim 1, said process further comprising hydrolyzing a portion of said cellulose-rich solids into glucose, recovering said glucose, and optionally fermenting said glucose to a fermentation product.

11. The process of claim 1, said process further comprising recovering, combusting, or further treating said lignin.

12. The process of claim 1, said process further comprising chemically converting said nanocellulose material to one or more nanocellulose derivatives selected from the group consisting of nanocellulose esters, nanocellulose ethers, nanocellulose ether esters, alkylated nanocellulose compounds, cross-linked nanocellulose compounds, acid-functionalized nanocellulose compounds, base-functionalized nanocellulose compounds, and combinations thereof.

13. The process of claim 1, wherein said digestion temperature is selected from 175° C. to 210° C.

14. The process of claim 1, wherein said digestion temperature is selected from 175° C. to 195° C.

\* \* \* \* \*